United States Patent [19]

Traxler

[11] 4,299,772
[45] Nov. 10, 1981

[54] XANTHENONE-YL ESTERS OF PHOSPHORIC AND PHOSPHONIC ACIDS

[75] Inventor: James T. Traxler, Evanston, Ill.

[73] Assignee: Velsicol Chemical Corporation, Chicago, Ill.

[21] Appl. No.: 127,007

[22] Filed: Mar. 4, 1980

[51] Int. Cl.³ .......................................... C07D 311/86
[52] U.S. Cl. ................................................. 260/335
[58] Field of Search ....................... 424/283; 260/335

[56] References Cited

U.S. PATENT DOCUMENTS 4,217,361  8/1980  Pfister ................................. 260/335

FOREIGN PATENT DOCUMENTS 2247268  4/1973  Fed. Rep. of Germany.

OTHER PUBLICATIONS

Mustafa et al., *Justus Liebiegs Ann. Chem.*, vol. 698, pp. 109-112 (1966); Chemical Abstracts, vol. 66, 75881j (1967).
Sidky et al., Chemical Abstracts, vol. 78, entry 71849 (1973).
Hurt, Chemical Abstracts, vol. 86, entry 189491 (1977).

*Primary Examiner*—John M. Ford
*Attorney, Agent, or Firm*—Dietmar H. Olesch; Robert J. Schwarz

[57] ABSTRACT

Disclosed are new compounds of the formula

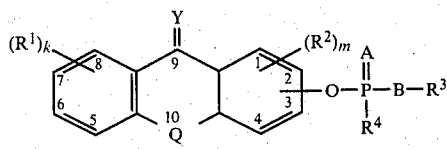

wherein $R^1$ and $R^2$ are each independently selected from the group consisting of halogen, alkyl, haloalkyl, nitro, alkylsulfinyl, alkylsulfonyl and cyano; k and m are integers from 0 to 3; Q is selected from the group consisting of oxygen and sulfur; Y is selected from the group consisting of oxygen and sulfur $R^3$ is selected from the group consisting of alkyl and

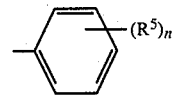

wherein $R^5$ is selected from the group consisting of halogen, alkyl, haloalkyl, nitro and cyano; n is an integer from 0 to 3; $R^4$ is selected from the group consisting of alkyl, alkoxy, alkylthio, amino, alkylamino, dialkylamino and

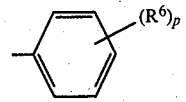

wherein $R^6$ is selected from the group consisting of halogen, alkyl, haloalkyl, nitro, and cyano; p is an integer from 0 to 3; and A and B are each independently selected from the group consisting of oxygen and sulfur, with the proviso that, if $R^4$ is alkoxy, then one of A and B must be sulfur.

Further disclosed is the insecticidal utility of the foregoing compounds.

11 Claims, No Drawings

XANTHENONE-YL ESTERS OF PHOSPHORIC AND PHOSPHONIC ACIDS

This invention related to new compositions of matter and more specifically relates to new chemical compounds of the formula

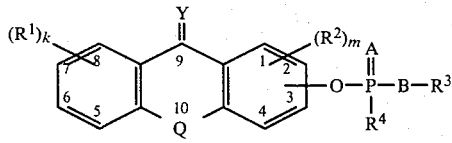

wherein $R^1$ and $R^2$ are each independently selected from the group consisting of halogen, alkyl, haloalkyl, nitro, alkylsulfinyl, alkylsulfonyl and cyano; k, and m are integers from 0 to 3; Q is selected from the group consisting of oxygen and sulfur; Y is selected from the group consisting of oxygen and sulfur; $R^3$ is selected from the group consisting of alkyl and

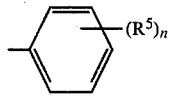

wherein $R^5$ is selected from the group consisting of halogen, alkyl, haloalkyl, nitro and cyano; n is an integer from 0 to 3; $R^4$ is selected from the group consisting of alkyl, alkoxy, alkylthio, amino, alkylamino, dialkylamino and

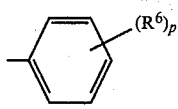

wherein $R^6$ is selected from the group consisting of halogen, alkyl, haloalkyl, nitro, and cyano; and p is an integer from 0 to 3;

and A and B are each independently selected from the group consisting of oxygen and sulfur, with the proviso that, if $R^4$ is alkoxy, then one of A and B must be sulfur.

These compounds are useful as insecticides.

In a preferred embodiment of this invention, $R^1$ and $R^2$ are each independently selected from the group consisting of halogen, lower alkyl, lower haloalkyl, nitro, lower alkylsulfinyl, lower alkylsulfonyl, and cyano; k and m are integers from 0 to 3; Q is selected from the group consisting of oxygen and sulfur; Y is selected from the group consisting of oxygen and sulfur; $R^3$ is selected from the group consisting of lower alkyl and

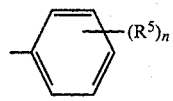

wherein $R^5$ is selected from the group consisting of halogen, lower alkyl, lower haloalkyl, nitro and cyano, n is an integer from 0 to 3; $R^4$ is selected from the group consisting of lower alkyl, lower alkoxy, lower alkylthio, amino lower alkylamino, di(lower alkyl) amino and

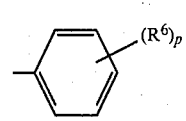

wherein $R^6$ is selected from the group consisting of halogen, lower alkyl, lower haloalkyl, nitro and cyano; p is an integer from 0 to 3; and A and B are each independently selected from the group consisting of oxygen and sulfur, with the proviso that, if $R^4$ is alkoxy, then one of A and B must be sulfur.

The term "lower" as used herein designates a straight or branched carbon chain of up to six carbon atoms.

The compounds of this invention can be made by reacting a compound of the formula

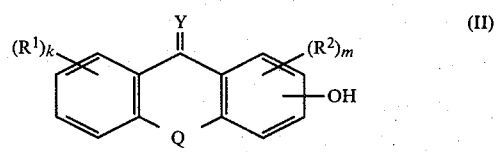

wherein $R^1$, $R^2$, k and m, Q, and Y are as hereinbefore described, with a compound of formula

wherein $R^3$, $R^4$, A and B are as hereinbefore described. This reaction can be effected by dissolving or slurrying, in an inert reaction medium such as acetonitrile or tetrahydrofuran, the compound of formula II together with an acid acceptor such as potassium carbonate or triethylamine. To this solution/slurry is then added, with stirring, at a temperature of from about 0° C. to 40° C., the compound of formula III. The reaction mixture may be stirred for a period of several hours after the addition to ensure completeness of reaction, the acid-acceptor salts can then be filtered off and the desired product isolated and purified by standard techniques.

The compound of formula II wherein Y is oxygen can be prepared by the following reaction sequence:

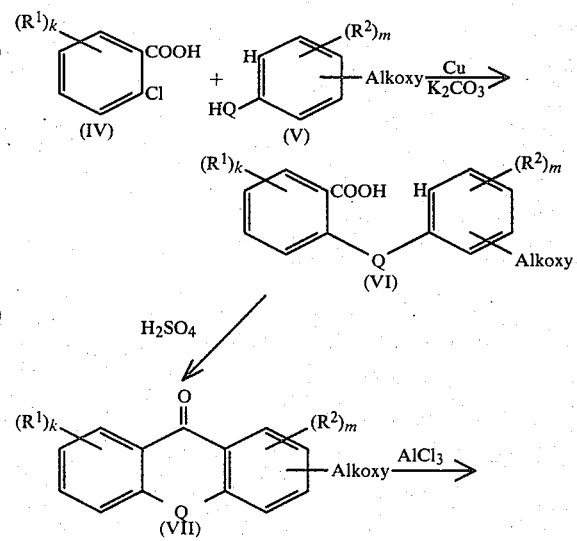

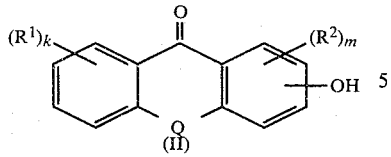

wherein $R^1$, $R^2$, k, m, and Q are as hereinabove described.

The alkoxy group of the compound of formula V may be any lower alkoxy but preferably is methoxy. Also, the formula V compound must have at least one hydrogen ortho to the —QH group.

The position of the hydroxyl group of the formula II compound is determined by the position of the alkoxy group relative to the —QH group of the formula V compound, thus this compound is selected to give a formula II compound having the desired structure. However, when both positions ortho to the —QH group of the formula V compound are hydrogen, a mixture of position isomers of the formula VII compound, and thus of the formula II compound, are produced. These isomers can be separated and the desired isomer of the formula II compound isolated by art-known methods such as fractional crystallization, differential solubilization, high performance liquid chromatography and the like.

In carrying out the above reaction sequence, the compounds of formula IV and V are dissolved in an inert reaction medium such as 1-pentanol, a copper catalyst (preferably prepared according to the method of P. H. Gore and G. K. Huges, Journal of the Chemical Society, 1615(1959), wherein copper metal is precipitated from copper sulfate solution by zinc dust) and potassium carbonate are added and the mixture is stirred and heated, at the reflux temperature of the solvent, for a period of from about 0.5 to about 8 hours.

Treatment of uncyclized condensation product, the formula VI compound, with concentrated sulfuric acid effects its cyclization to the compound of formula VII. An inert reaction medium, such as acetyl chloride is used, the reaction is carried out at room temperature or slightly elevated temperatures for a period of from about 0.5 to 2 hours.

The compound of formula II is generally known in the art and may be prepared by treatment of the compound of formula VII, in an inert reaction medium such as toluene, with anhydrous aluminum chloride at a temperature of from 80° C. to 90° C. for a period of from about 2 to 4 hours. Hydrochloric acid, at a concentration of about 6 N is then added and the mixture stirred at a temperature of from 80° C. to 90° C. for a period of from about 2 to 4 hours.

The compound of formula II wherein Y is sulfur may be prepared by the reaction sequence:

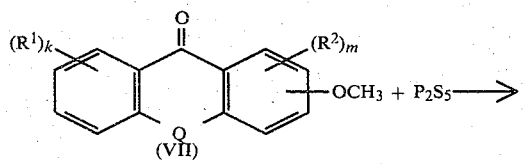

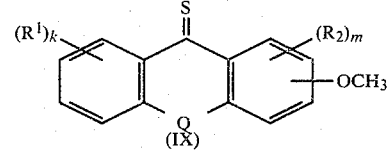

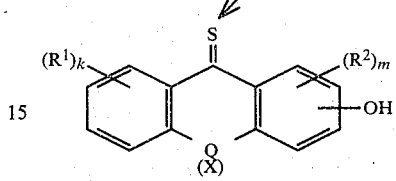

wherein $R^1$, $R^2$, k, m, and Q are as heretofore described. The compound of formula VII is mixed, with no diluents, with $P_2S_5$ and heated to a temperature of from about 130° C. to 140° C. for a period of from about 0.5 to 4 hours. The unreacted $P_2S_5$ is removed by hydrolysis with water; the compound of formula IX may then be recrystallized using, for example, ethanol. The formula X compound may be prepared by treating the formula IX compound with anhydrous aluminum chloride as described hereinabove for the preparation of the formula II compound from the formula VII compound.

Exemplary compounds of formula III suitable for preparing the compounds of the present invention are O-ethyl S-propyl phosphorochloridothiolate; O-ethyl S-propyl phosphorochloridothiolothionate; O-(2,4-dicyanophenyl) S-propyl phosphorochloridothiolate; O-(3,4,5-trichlorophenyl) S-propyl phosphorochloridothiolothionate; S-ethyl S-propyl phosphorochloridothiolate; S-butyl S-pentyl phosphorochloridodithiolothionate; S-pentyl ethylphosphonochloridothiolate; S-(3-nitrophenyl) (3-chlorophenyl) phosphonochloridothiolothionate; O-(2,3-dimethylphenyl) S-butyl phosphorochloridothiolate; O-ethyl O-butyl phosphorochloridothionate; O-(4-chloro-5-methylphenyl) O-propyl phosphorochloridothionate; O-ethyl S-propyl phosphorochloridothiolothionate; O-ethyl ethylphosphonochloridothiolate; O-ethyl N,N-diemthylphosphoramidochloridate; S-propyl N,N-diethylphosphoramidochloridothiolate; S-pentyl N,N-dihexylphosphoramidothiolothionate; O-butyl N-butylphosphoramidochloridate; S-hexyl phosphoramidochloridothiolate and the like.

Exemplary compounds of formula IV suitable for preparation the compounds of the present invention are 2-chlorobenzoic acid; 2-chloro-3-cyanobenzoic acid; 2-chloro-4,5-dimethylbenzoic acid; 2,3,5-trichlorobenzoic acid; 2-chloro-4-(trifluoro-methyl) benzoic acid; 2-chloro-2-methyl-3-ethylsulfinylbenzoic acid; 2,3,4-trichloro-4-ethyl-sulfonylbenzoic acid; 2,4-dichloro-3-methyl-4-chloro-5-cyanobenzoic acid; 2-chloro-5-nitrobenzoic acid and the like.

Exemplary compounds of formula V suitable for preparing the compounds of this invention are 2-methoxyphenol; 2-methoxy-3,4-dichlorophenol; 2-methoxy-4,5-dimethylphenol; 2-methoxy-5-nitrophenol; 2-methoxy-3-(trifluoromethyl)phenol; 2-methoxy-4-ethylsulfinylphenol; 2-methoxy-3,5-dicyanophenol; 2-methoxy-3,4,5-tribromophenol; 2-methoxy-4-ethylsulfonylphenol; 2-methoxy-4-cyanobenzenethiol; 2-methoxy-3,4-dinitrobenzenethiol;

2-methoxy-3-trichloromethyl-4-ethylbenzenethiol; 2-methoxy-4-ethylsulsulfinylbenzenethiol; 2-methoxy-4-methyl-5-propylsulfonylbenzenethiol; 2-methoxy-3,4-dichlorobenzenethiol; 3-methoxy-4-bromophenol; 3-methoxy-5,6-dinitrophenol; 3-methoxy-4,5-dicyanophenol; 3-methoxy-4-butylsulfinylphenol; 3-methoxy-5-ethyl-6-(trifluoromethyl)phenol; 3-methoxy-4-propylsulfonyl-phenol; 2,5-dibromo-3-methoxyphenol; 3-methoxyphenol; 2,4-dichloro-3-methoxybenzenethiol; 2,5-dicyano-3-methoxybenzenethiol; 3-methoxy-5-butylsulfonylbenzenethiol; 3-methoxy-4,5,6-trichlorobenzenethiol; 2-trifluoromethyl-3-methoxybenzenethiol; 3-methoxy-5-butylsulfinylbenzenethiol; 4-methoxyphenol; 2-chloro-3-ethyl-4-methoxyphenol; 3-nitro-4-methoxyphenol; 2-(1-ethylpropyl)-3-cyano-4-methoxyphenol; 2,3-dibutyl-4-methoxyphenol; 3-ethylsulfonyl-4-methoxyphenol; 4-methoxy-5-butylsulfonylphenol; 4-methoxy-5-trifluoromethylphenol; 2,3-dichloro-5-(2-ethylbutyl)benzenethiol; 3-cyano-4-methoxybenzenethiol; 2-ethyl-3-(trifluoromethyl)benzenethiol; 3-nitro-4-methoxybenzenethiol; 2-propylsulfinyl-4-methoxybenzenethiol; 3-bromo-4-methoxy-5-ethylsulfonylbenzenethiol and the like.

EXAMPLE 1

PREPARATION OF O,O-Diethyl O-(Xanthen-9-one-2-yl) Phosphorothionate

2-Hydroxyxanthen-9-one (1.0 gram; 0.0047 mole), O,O-diethyl-phosphorochloridothionate (0.89 grams; 0.0049 mole), acetonitrile (25 ml) and potassium carbonate (1.94 grams; 0.0047 mole) were charged into a glass reaction vessel fitted with a mechanical stirrer and thermometer. The reaction mixture was then stirred at a temperature of from about 40° C. to 45° C. for a period of about 16 hours. A precipitate formed which was filtered off, washed with acetonitrile and the washings added to the filtrate. An equal volume of acetonitrile was added to the combined acetonitrile solutions and silica gel (2 grams) added and the slurry stirred at room temperature for a period of about 1.5 hours. The silica gel was filtered off, the filtrate was treated with activated charcoal, refiltered and the solvent stripped off on a rotary evaporator (70° C., 15 mm Hg) to give a brown oil. This oil was dissolved in a 1/1 mixture of chloroform/cyclohexane (16 ml), silica gel (2 grams) was added and the slurry was stirred for 2.5 hours at room temperature. The silica gel was filtered off, washed with toluene and the washings combined with the filtrate. Solvent was then stripped from the filtrate to yield the desired product O,O-diethyl O-(xanthen-9-one-2-yl) phosphorothionate.

Elemental analysis; Theory: C=56.04%; H=4.70%; P=8.50%. Found: C=55.76%; H=4.73%; P=8.5%.

EXAMPLE 2

PREPARATION OF O-Ethyl O-(Xanthen-9-one-2-yl) S-Propyl Phosphorothiolate

2-Hydroxyxanthen-9-one (1.4 grams; 0.0066 mole) was slurried in methylene chloride (10 ml) and added dropwise over about a 5 minutes period to a solution of O-ethyl S-propyl phosphorochloridothiolate in methylene chloride (15 ml), at a temperature of about 0° C., contained in a glass reaction vessel fitted with a mechanical stirrer and thermometer. The reaction mixture was then cooled to about −65° C. and triethylamine (0.67 grams) in methylene chloride (2 ml) added. The reaction mixture was stirred at a temperature of about 10° C. for a period of about 2 hours. After holding at room temperature for a period of about 16 hours, the mixture was diluted with an equal volume of methylene chloride and this solution washed with cold H₂O (3–30 ml portions), dried with phase separation paper, treated with activated carbon and filtered. The solvent was stripped off on a rotary evaporator (70° C., 15 mm Hg) to yield a brown oil which solidified. This oil was added to 5 volumes of diisopropyl ether and the mixture heated to reflux, cooled and filtered. The ether was stripped off in a rotary evaporator to yield a yellow oil. The yellow oil was dissolved in a solvent comprised of 60 volumes chloroform, 40 volumes cyclohexane. Silica gel (2 grams) was added to this solution and the mixture was stirred for a period of about 1 hour at room temperature, then filtered. The silica gel was washed with 60/40 v/v chloroform/cyclohexane (1.0 ml) and the washings combined with the filtrate. Solvent was partially stripped off with a rotary evaporator, and the concentrate was chromatographed on a silica gel column using as eluent 40/60 v/v ethyl acetate/cyclohexane. The fractions containing the desired product were identified by infrared and NMR analysis. These fractions were combined and the solvent stripped off on a rotary evaporator to yield the desired product O-ethyl O-(xanthen-9-one-2-yl) S-propyl phosphorothiolate as a light yellow oil which crystallized on standing.

Elemental analysis; Theory: C=57.13%; H=5.06%; P=8.19%. Found: C=57.13%; H=5.10%; P=7.75%.

EXAMPLE 3

PREPARATION OF O-Phenyl O-(Xanthen-9-one-2-yl) S-Propyl Phosphorothiolate

2-Hydroxyxanthen-9-one (0.01 mole), acetonitrile (25 ml) and potassium carbonate (0.01 mole) are charged into a glass reaction vessel fitted with a mechanical stirrer and thermometer. O-Phenyl S-propyl phosphorochloridothiolate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with silica gel (2 grams) at room temperature for a period of about 2 hours, then filtered. Solvent is stripped from the filtrate using a rotary evaporator to yield the desired product O-phenyl O-(xanthen-9-one-2-yl) S-propyl phosphorothiolate.

EXAMPLE 4

PREPARATION OF O-(Xanthen-9-one-2-yl) S-Nitrophenyl) S-Propyl Phosphorodithiolate 2-Hydroxyxanthen-9-one (0.01 mole), acetonitrile (25 ml) and potassium carbonate (0.01 mole) are charged into a glass reaction vessel fitted with a mechanical stirrer and thermometer. S-(4-Nitrophenyl) S-propyl phosphorochlorododithiolate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with silica gel (2 grams) at room temperature for a period of about 2 hours, then filtered. Solvent is stripped from the filtrate using a rotary evaporator to yield the desired product O-(xanthen-9-one-2-yl) S-(nitrophenyl) S-propyl phosphorodithiolate.

EXAMPLE 5

PREPARATION OF O-Ethyl O-(Xanthen-9-thione-2-yl) S-Propyl Phosphorothiolothionate 2-Hydroxyxanthen-9-thione (1.97 grams; 0.009 mole) and acetonitrile (120 ml) were charged into a glass reaction vessel fitted with a mechanical stirrer, thermometer and reflux condenser, and the xanthenethione put into solution by heating to reflux for a period of about 1 hour. The solution was cooled to room temperature, then treated with activated carbon, filtered, and charged into a glass reaction vessel fitted with a mechanical stirrer and thermometer. Potassium carbonate (1.2 grams) and O-ethyl S-propyl phosphorochloridothiolothionate (1.74 grams) were added to the reaction vessel and the mixture was stirred at a temperature of from about 30° C. to 35° C. for a period of about 24 hours. The reaction mixture was then warmed to a temperature of about 50° C. and stirred for an additional period of about 7 hours. The reaction mixture was filtered and the solvent was stripped from the filtrate using a rotary evaporator (70° C., 15 mm Hg) to give an oil. This oil was dissolved in a solvent comprised of 6.5 volumes chloroform, 93.5 volumes cyclohexane (40 ml); silica gel (4 grams) was added and the mixture stirred at room temperature for a period of about 2.5 hours. The solution was filtered, the filtrate treated with activated carbon and refiltered. The solvent was stripped off on a rotary evaporator to yield the desired product O-ethyl O-(xanthen-9-thione-2-yl) S-propyl phosphorothiolothionate.

Elemental Analysis: Theory: C=52.67; H=4.66; p=7.55. Found: C=52.25; H=4.68; P=7.37.

EXAMPLE 6

PREPARATION OF O-(Xanthen-9-thione-2-yl) S-Ethyl Phenylphosphonothiolate

2-Hydroxyxanthen-9-thione (0.01 mole), acetonitrile (25 ml) and potassium carbonate (0.01 mole) are charged into a glass reaction vessel fitted with a mechanical stirrer and thermometer. S-Ethyl phenylphosphonochloridothiolate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 chloroform/cyclohexane (25 ml). This solution is then slurried with silica gel (2 grams) at room temperature for a period of about 2 hours, then filtered. Solvent is stripped from the filtrate using a rotary evaporator to yield the desired product O-(xanthen-9-thione-2-yl) S-ethyl phenylphosphonothiolate.

EXAMPLE 7

PREPARATION OF O-Ethyl O-(Xanthen-9-thione-2-yl) S-Propyl Phosphorothiolate

2-Hydroxyxanthen-9-thione (0.01 mole), acetonitrile (25 ml) and potassium carbonate (0.01 mole) are charged into a glass reaction vessel fitted with a mechanical stirrer and thermometer. O-Ethyl S-propyl phosphorochloridothiolate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 chloroform/cyclohexane (25 ml). This solution is then slurried with silica gel (2 grams) at room temperature for a period of about 2 hours, then filtered. Solvent is stripped from the filtrate using a rotary evaporator to yield the desired product O-ethyl O-(xanthen-9-thione-2-yl) S-propyl phosphorothiolate.

EXAMPLE 8

PREPARATION OF O-Ethyl O-(Xanthen-9-one-3-yl) S-Propyl Phosphorothiolothionate 3-Hydroxyxanthen-9-one (1.48 grams; 0.007 moles) and acetonitrile (20 ml) were charged into a glass reaction vessel fitted with a mechanical stirrer and thermometer. To this mixture, at room temperature, was added potassium carbonate (0.97 grams, 0.007 mole) and a solution of O-ethyl S-propyl phosphorochloridothiolothionate (1.41 grams; 0.007 mole) in acetonitrile. The reaction mixture was stirred for a period of about 54 hours at a temperature of about 50° C. The reaction mixture was cooled to room temperature and filtered. The filtered-off solid was washed with acetonitrile (10 ml) and the washings combined with filtrate. The combined filtrate/washings were concentrated on a rotary evaporator to give a yellow brown oil. This oil was dissolved in acetone (5 ml), cyclohexane (95 ml) was added, then 5 grams of silica gel. The mixture was stirred for a period of 1 hour at room temperature, filtered, the silica gel washed with 5/95 v/v acetone/cyclohexane, the washings combined with the filtrate and the solvent removed from the combined filtrate/washings on a rotary evaporator to yield the desired product O-ethyl O-(xanthen-9-one-3-yl) S-propyl phosphorothiolothionate as a yellow oil.

Elemental Analysis; Theory: C=54.86%; H=4.85%; P=7.85%. Found: C=55.57%, H=4.99%, P=7.41.

EXAMPLE 9

PREPARATION OF O-Ethyl O-(Xanthen-9-one-3-yl) S-(3,5-Dichlorophenyl)phosphorothiolothionate 3-Hydroxyxanthen-9-one (0.01 mole), acetonitrile (25 ml) and potassium carbonate (0.01 mole) are charged into a glass reaction vessel fitted with a mechanical stirrer and thermometer. O-Ethyl S-(3,5-dichlorophenyl)phosphorothiolothionate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with silica gel (2 grams) at room temperature for a period of about 2 hours, then filtered. Solvent is stripped from the filtrate using a rotary evaporator to yield the desired product O-ethyl O-(xanthen-9-one-3-yl) S-(3,5-dichlorophenyl)phosphorothiolothionate.

EXAMPLE 10

PREPARATION OF O-(Xanthen-9-one-4-yl) S-Phenyl Phenylphosphonothiolothionate 4-Hydroxyxanthen-9-one (0.01 mole), acetonitrile (25 ml) and potassium carbonate (0.01 mole) are charged into a glass reaction vessel fitted with a mechanical stirrer and thermometer. S-Phenyl phenylphosphonochloridothiolothionate. (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with Silica Gel (2 grams) at room temperature for a period of about 2 hours, then filtered. Solvent is stripped from the filtrate using a rotary evaporator to yield the desired product O-(xanthen-9-one-4-yl) S-phenyl phenylphosphonotiolotionate.

EXAMPLE 11

PREPARATION OF O-Ethyl O-(Xanthen-9-one-4-yl) (2,4,6-Trichlorophenyl)phosphonate 4-Hydroxyxanthen-9-one (0.01 mole), acetonitrile (25 ml) and potassium carbonate (0.01 mole) are charged into a glass reaction vessel fitted with a mechanical stirrer and thermometer. O-Ethyl (2,4,6-trichlorophenyl)phosphonochloridate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with silica gel (2 grams) at room temperature for a period of about 2 hours, then filtered. Solvent is stripped from the filtrate using a rotary evaporator to yield the desired product O-ethyl O-(xanthen-9-one-4-yl) (2,4,6-trichlorophenyl)phosphonate.

EXAMPLE 12

PREPARATION OF O-Ethyl O-(3,6-Dimethylxanthen-9-one-2-yl) S-Propyl Phosphorothiolothionate 2-Hydroxy-3,6-dimethylxanthen-9-one (0.01 mole), acetonitrile (25 ml) and potassium carbonate (0.01 mole) are charged into a glass reaction vessel fitted with a mechanical stirrer and thermometer. O-Ethyl S-propyl phosphorochloridothiolothionate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with silica gel (2 grams) at room temperature for a period of about 2 hours, then filtered. Solvent is stripped from the filtrate using a rotary evaporator to yield the desired product O-ethyl O-(3,6-dimethylxanthen-9-one-2-yl) S-propyl phosphorothiolothionate.

EXAMPLE 13

PREPARATION OF O-(3,6-Dimethylxanthen-9-one-2-yl) S-Ethyl (2,6-Dicyanophenyl)phosphonothiolothionate 2-Hydroxy-3,6-dimethylxanthen-9-one (0.01 mole), acetonitrile (25 ml) and potassium carbonate (0.01 mole) are charged into a glass reaction vessel fitted with a mechanical stirrer and thermometer. S-Ethyl (2,6-dicyanophenyl)phosphonochloridothiolothionate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with silica gel (2 grams) at room temperature for a period of about 2 hours, then filtered. Solvent is stripped from the filtrate using a rotary evaporator to yield the desired product O-(3,6-dimethylxanthen-9-one-2-yl) S-ethyl (2,6-dicyanophenyl)phosphonothiolothionate.

EXAMPLE 14

PREPARATION OF O-Hexyl O-(3-Nitroxanthen-9-one-4-yl) S-(2-Methyl-4-bromophenyl)Phosphorothiolothionate 3-Nitro-4-hydroxyxanthen-9-one (0.01 mole), acetonitrile (25 ml) and potassium carbonate (0.01 mole) are charged into a glass reaction vessel fitted with a mechanical stirrer and thermometer. O-Hexyl S-(2-methyl-4-bromophenyl)phosphorochloridothiolothionate (0.01 mole) in acetonitrile (6 ml) is added dropwsie, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with silica gel (2 grams) at room temperature for a period of about 2 hours, then filtered. Solvent is stripped from the filtrate using a rotary evaporator to yield the desired product O-hexyl O-(3-nitroxanthen-9-one-4-yl) S-(2-methyl-4-bromophenyl)phosphorothiolothionate.

EXAMPLE 15

PREPARATION OF O-(3-Nitroxanthen-9-one-4-yl) S-Ethyl (4-Trifluoromethylphenyl)phosphonothiolothionate 3-Nitro-4-hydroxyanthen-9-one (0.01 mole), acetonitrile (25 ml) and potassium carbonate (0.01 mole) are charged into a glass reaction vessel fitted with a mechanical stirrer and thermometer. S-Ethyl (4-trifluoromethylphenyl)phosphonochloridothiolothionate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with silica gel (2 grams) at room temperature for a period of about 2 hours, then filtered. Solvent is stripped from the filtrate using a rotary evaporator to yield the desired product O-(3-nitroxanthen-9-one-4-yl) S-ethyl (4-trifluromethylphenyl)phosphonothiolothionate.

EXAMPLE 16

PREPARATION OF O-Ethyl O-(4-Cyanoxanthen-9-one-3-yl) 4-Chlorophenylphosphonothionate 1-Hydroxy-4-nitro-6-cyanoxanthen-9-one (0.01 mole), acetonitrile (25 ml) and potassium carbonate (0.01 mole) are charged into a glass reaction vessel fitted with a mechanical stirrer and thermometer. O-Ethyl (4-chlorophenyl)phosphonochloridothionate (0.01 mole) in acetonitrile (6 ml) is added dropwise, with stirring, at room temperature. The reaction mixture is stirred for a period of about 48 hours at a temperature of from about 35° C. to 50° C. It is then cooled to room temperature and filtered. Solvent is stripped from the filtrate using a rotary evaporator (70° C., 15 mm Hg). The devolatilized residue is redissolved in 1/1 v/v chloroform/cyclohexane (25 ml). This solution is then slurried with silica gel (2 grams) at room temperature for a period of about 2 hours, then filtered. Solvent is stripped from the filtrate using a rotary evaporator to yield the desired product O-ethyl O-(4-nitro-6-cyanoxanthen-9-one-1-yl) 4-chlorophenylphosphonothionate.

EXAMPLE 17

PREPARATION OF O-Ethyl O-(Thioxanthen-9-one-2-yl) S-Propyl Phosphorothiolothionate 2-Hydroxythioxanthen-9-one (2.28 grams; 0.01 mole), acetonitrile (60 ml) and potassium carbonate (1.38 grams; 0.01 mole) were charged into a glass reaction vessel fitted with a mechanical stirrer and thermometer. O-Ethyl S-propyl phosphorochloridothiolothionate (2.18 grams; 0.01 mole) in acetonitrile (3 ml) was added dropwise, with stirring, at room temperature. The reaction mixture was stirred for a period of about 30 hours at room temperature. After this time the reaction mixture was filtered and the filtrate stripped of solvent using a rotary evaporator. The residue was then column chromatographed using silica gel and a 25/75 mixture of ethyl acetate and cyclohexane. The eluant is stripped of solvent to yield the desired product O-ethyl O-(thioxanthen-9-one-2-yl) S-propyl phosphorothiolothionate as an oil.

EXAMPLE 18

PREPARATION OF O-Ethyl O-(Thioxanthen-9-one-2-yl) S-Propyl Phosphorothiolate 2-Hydroxythioxanthene-9-one (2 grams; 0.009 mole), toluene (25 ml) tetrahydrofuran (25 ml) and triethylanine (0.89 grams) were charged into a reaction vessel equipped with stirrer and thermometer. The mixture was cooled to 0° C. and O-ethyl S-propyl phosphorochloridothiolate (0.009 mole) dissolved in toluene (16 ml) was added dropwise with stirring. After the addition was completed, the mixture was allowed to stand at room temperature overnight. The mixture was then filtered, stripped of solvent and the residue was column chromatographed using a 40/60 ethyl acetate-cyclohexane mixture. The eluant was stripped of solvents to yield the desired product. O-ethyl O-(thioxanthen-9-one-2-yl) S-propyl phosphorothiolate as an oil which solidified upon standing to a solid melting at 57° to 60° C.

Additional compounds within the scope of this invention which can be prepared according to the procedures of the foregoing examples are O-ethyl O-(5-trifluoromethylxanthen-9-one-2-yl) S-propyl phosphorothiolothionate; O-(2-chlorophenyl) O-(7-ethylsulfonylxanthen-9-one-2-yl) S-propyl phosphorothiolothionate; O,O-dipropyl O-(6-butylsulfinylxanthen-9-one-2-yl)phosphorothionate; O-ethyl O-(2-chloro-7-nitroxanthen-9-one-4-yl) S-propyl phosphorothiolothionate; O-(3-nitrophenyl) O-(2-chloro-6-nitro-7-ethylxanthen-9-one-4-yl) S-propyl phosphorothionate; O-ethyl O-(3-chloroxanthen-9-one-2-yl) S-propyl phosphorothiolate; O-ethyl O-(xanthen-9-thione-2-yl) S-propyl phosphorothiolothionate; O-ethyl O-(3-chloroxanthen-9-thione-2-yl) S-propyl phosphorothiolate; O-(3,4-dimethyl-7-cyanoxanthen-9-one-1-yl) S-pentyl S-hexyl phosphorothiolothionate; O-ethyl O-(4-ethylsulfinyl-8-ethylxanthen-9-one-2-yl) S-propyl phosphorothiolothionate; O-hexyl O-(1,4,6,7-tetramethylxanthen-9-one-3-yl) S-butyl phosphorothiolate; O-(2,7-dicyanoxanthen-9-one-4-yl) S-ethyl phenylphosphonothiolothionate; O-ethyl O-(2-nitro-6,7-dichloroxanthen-9-one-2-yl) S-propyl phosphorothiolothionate; O-(1,4-dimethyl-5,8-dinitroxanthen-9-one-3-yl) S-ethyl S-propyl phosphorothiolothionate; O-(6,7-dimethylxanthen-9-thione-2-yl) S-ethyl S-propyl phosphorodithiolothionate; O-(4-nitro-5-cyano-6-chloroxanthen-9-thione-1-yl) S-butyl S-pentyl phosphorodithiolothionate; O-ethyl O-(1,4-dipropyl-6,7-dichloroxanthen-9-thione-2-yl) S-propyl phosphorothiolothionate; O-methyl O-(4-cyano-6,7-dichloroxanthen-9-thione-3-yl) S-butyl phosphorothionate; O-(6,7,8-trimethylxanthen-9-thione-4yl) S-ethyl S-butyl phosphorodithiolate; O-ethyl O-(4-trifluoromethylxanthen-9-thione-2-yl) S-propyl phosphorothiolothionate; O-ethyl O-(6-ethylsulfonylxanthen-9-thione-1-yl) S-propyl phosphorothiolothionate; O-(8-propylsulfinylxanthen-9-thione-2-yl) S,S-dipropyl phosphorodithiolothionate; O-ethyl O-(xanthen-9-one-2-yl) S-propyl phorothiolothionate; O-pentyl O-(2-ethyl-6-chloroxanthen-9-one-1-yl) S-propyl phosphorothiolothionate; O-ethyl O-(5-chloroxanthen-9-one-2-yl) N,N-dimethylphosphoramidate; O-(6-methylxanthen-9-one-2-yl) S-butyl N,N-dipentylphosphoramidothiolate; O-(8-ethylsulfinylxanthen-9-one-2-yl) S-hexyl N-propylphosphoramidothiolate; O-(2-butylxanthen-9-one-2-yl) S-propyl phosphoramidothiolothionate and the like.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvent such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect infestation. The emulsifiers most commonly used in these concentrates are nonionic or mixture of nonionic with anionic surface-active agents.

A typical insecticidal composition according to this invention is illustrated by the following example, in which the quantities are in parts by weight.

EXAMPLE 19

| Preparation of a Dust | |
|---|---|
| Product of Example 1 | 10 |
| Powdered talc | 90 |

The above ingredients are mixed in a mechanical grinder-blender and are ground until a homogeneous, freeflowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol and the like; organic phosphorus compounds such as TEPP, schradan, ethion, parathion, methyl parathion, PEN, demeton, carbophenothion phorate, zinophos, diazinon, malathion, mevinphos, dimethoate, DBD, ronnel, oxydemeton-methyl, dicapthon, chlorothion, phosphamidon, naled, fenthion, trichlorofon, DDVP and the like; organic nitrogen compounds such as dinitro-O-cresol, dinitrocyclohexylphenol, DNB, DNP, binapacril, azobenzene and the like; organic carbamate compounds such as carbaryl, ortho 5353 and the like; organic sulfur compounds such as phenothiazine, phenoxathin, lauryl thiocyanate, bis(2-thiocyanoethyl)ether, isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like; while examples of nematocidal compounds are chloropicrin O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plants surfaces are taken up by the plant, and the insects are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms of weevils such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the woolly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

The insecticidal activity of the compounds of the present invention was demonstrated by experiments carried out for the control of a variety of insects. The desired quantity of the test compound (the coquantity being determined by the application concentration or application rate to be used in later testing) is dissolved or dispersed in a solvent consisting of acetone containing 3.19 grams/liter of Triton X-155 ® (alkylaryl polyether alcohol). When it has dissolved or dispersed in the acetone, 4 volumes of the acetone solution or dispersion are diluted with 96 volumes of distilled water. (If the test compound is insoluble in the acetone or distilled water it can be dispersed using a tissue grinder.) Lower concentration test solutions may be made by dilution of higher concentration solutions with a diluent consisting of 96 volumes distilled water and 4 volumes of acetone containing 3.19 grams of Triton X 155 ® per liter.

Test plants used in these experiments are prepared by planting the appropriate seeds in sterilized soil contained in plastic pots having an upper soil surface area of approximately 12.25 square inches (a square pot having a 3.5 inch side). After the seed has been planted, a layer of approximately 0.25 inches of sand is spread on the top surface of the soil. The test compound is applied after the plant has reached a specified size.

For foliar applications, the test compound, dissolved or dispersed in the water/acetone solvent described above, is sprayed as a mist onto the foliage of the test plants. The concentration of the test compound and the total quantity of solution applied is adjusted to give the application concentrations or rates desired. The plants are then allowed to air dry. Mites and aphids are exposed to treated leaves which have been left on the plant. Other insect species are exposed to treated leaves which have been removed from the plant and placed in petri dishes containing a piece of moist filter paper.

For soil drench applications, the test compound is first dissolved or dispersed in water/acetone as described above, then the amount of solution required to give a desired application rate is applied, using a pipette, evenly over the top of the soil in the pot. Twenty four hours after the treatment, mites and aphids are exposed to leaves which have been left on the treated plants. Other insect species are exposed to leaves which have been removed from the plants 24 hours after treatment and placed in petri dishes containing a piece of moist filter paper.

In direct contact applications, the test compound is, again, first formulated into a water/acetone solution, as described above, in the concentrations to be tested. Then the insect to be tested is dipped into, sprayed with or immersed in the liquid, dried, and observed for effect.

In the tables below setting forth the experimental data where application rates are given in PPM(parts-per-million), the test formulations are applied either directly to insects or as foliar sprays to plants. Where application rates are given in #/A (pounds per acre) the test formulations are applied as soil drenches. Percent control is the percent mortality of the insects tested.

CABBAGE LOOPER

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten cabbage loopers, second instar larval stage, are placed in each petri dish and the dish covered. Observations of insect mortality are made after 48 hours of exposure. Results of these tests are detailed in Table 1 below.

TABLE 1

| Test Compound | Application Rate: PPM #/A | 256 | 128 | 64 | 32 | 16 | 32 | 16 | 8 | 4 | 2 |
|---|---|---|---|---|---|---|---|---|---|---|---|
| | | | | | | | Percent Control | | | | |
| Product of Example 1 | | 0 | — | — | — | — | 10 | — | — | — | — |
| Product of Example 2[1] | | 90 | 40[2] | 5 | 0 | 0 | 0 | 0 | 10 | 5 | 5 |
| Product of Example 18 | | 100 | 100 | 90 | 100 | 70 | — | — | — | — | — |

Note:
[1] average of 2 tests
[2] Living insects stunted

SOUTHERN ARMYWORM

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten southern armyworms, second instar larval stage, are placed in each petri dish and the dish covered. Observations of insect mortality are made after 48 hours of exposure. Results of these test are detailed in Table 2 below.

TABLE 2

| Test Compound | Application Rate: PPM #/A | 256 | 128 | 64 | 32 | 16 | Percent Control 32 | 16 | 8 | 4 | 2 |
|---|---|---|---|---|---|---|---|---|---|---|---|
| Product of Example 1 | | 0 | — | — | — | — | 20 | — | — | — | — |
| Product of Example 2[1] | | 100 | 95 | 65[2] | 15[2] | 10 | 5 | 10 | 0 | 15 | 0 |
| Product of Example 18 | | 100 | 100 | 100 | 90 | 70 | — | — | — | — | — |

[1] average of 2 tests
[2] Living insects stunted

SOYBEAN LOOPER

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dish containing a piece of moist filter paper. Ten second instar larval soybean loopers are placed in each petri dish and the dish covered. Observations of insect mortality are made after 48 hours of exposure. Results of these test are detailed in Table 3 below.

TABLE 3

| Test Compound | Application Rate: PPM #/A | 256 | 128 | 64 | 32 | 16 | Percent Control 32 | 16 | 8 | 4 | 2 |
|---|---|---|---|---|---|---|---|---|---|---|---|
| Product of Example 1 | | 0 | — | — | — | — | 0 | — | — | — | — |
| Product of Example 2[1] | | 80[2] | 50[2] | 25[2] | 0 | 0 | 0 | 5 | 0 | 0 | 5 |
| Product of Example 18 | | 100 | 100 | 100 | 50 | 0 | — | — | — | — | — |

[1] average of 2 tests
[2] Living insects stunted

TOBACCO BUDWORM

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten tobacco budworms, second instar larval stage, are placed in each petri dish and the dish covered. Observations of insect mortality are made after 48 hours of exposure. Results of these tests are detailed in Table 4 below.

TABLE 4

| Test Compound | Application Rate: PPM #/A | 256 | 128 | 64 | 32 | 16 | 32 | 16 | 8 | 4 | 2 |
|---|---|---|---|---|---|---|---|---|---|---|---|
| Product of Example 4 | | 0 | — | — | — | — | 0 | — | — | — | — |
| Product of Example 5[1] | | 95[2] | 65[2] | 25[2] | 20[2] | 0 | 5 | 0 | 10 | 5 | 15 |
| Product of Example 18 | | 90 | 70 | 50 | 10 | 10 | — | — | — | — | — |

Note:
[1] average of 2 tests
[2] Living insects stunted

MEXICAN BEAN BEETLE

Bush lima bean plants (Burpee Variety 222), two-leaf stage, are exposed, at various application rates, to the test compound applied both by the foliar spray and soil drench techniques. Leaves are removed from the plants—after approximately 30 minutes of airdrying for the foliar spray application, after 24 hours for the soil drench application—and placed in petri dishes containing a piece of moist filter paper. Ten mexican bean beetles second instar larval stage, are placed in each petri dish and the dish covered. Observations of insect mortality are made after 48 hours of exposure. Results of these tests are detailed in Table 5 below.

TABLE 5

| Test Compound | Application Rate: PPM #/A | 256 | Percent Control 32 |
|---|---|---|---|
| Product of Example 1 | | 10 | 0 |

BOLL WEEVIL

Cotton plants (Deltapine 16), two leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten adult boll weevils are placed in each petri dish and the dish is then covered. Observations of insect mortality are made after 48 hours of exposure. Results of these tests are detailed in Table 6 below.

TABLE 6

| Test Compound | Application Rate: PPM #/A | 256 | Percent Control 32 |
|---|---|---|---|
| Product of Example 1 | | 10 | 10 |

PEA APHID

Pea plants (Burpee Wando) in the 10–14 day stage are treated with the test compound, at various application rates, both by foliar spray and soil drench methods. The plants are air dried for about 30 minutes after the foliar spray is applied, then 25–50 pea aphids, adults and nymphs, are put on each treated plant and on an untreated control plant with a small paint brush. Twenty four hours after a plant has been treated by the soil drench method, it is infested by 25–50 aphids using the technique described above. An untreated control plant is similarly infested. After 48 hours of exposure of the insects to the treated plants, insect mortality is determined by comparison of the number of insects on the treated plants to the number on the untreated control plant. Results of this testing are set forth in Table 7 below.

TABLE 7

| Test Compound | Application Rate: PPM #/A | Percent Control 256 | 32 |
|---|---|---|---|
| Product of Example 1 | | 0 | 0 |

TWO SPOTTED MITE

Bush lima bean plants (Burpee Variety 222) in the two-leaf stage are treated with the test compound, at various application rates, both by the foliar spray and soil drench methods. The plants are air dried for about 30 minutes after the foliar spray is applied, then 50–100 two spotted mites, adults and nymphs, are put on each treated plant and on an untreated control plant by placing an untreated infested bean leaf containing 50–100 mites on the plants. Twentyfour hours after a plant has been treated by the soil drench method, it is infested by 50–100 mites using the technique described above. An untreated control plant is similarly infested. After 48 hours of exposure of the insects to the treated plants, insect mortality is determined by comparison of the number of insects on the treated plants to the number on the untreated control plant. Results of this testing are set forth in Table 8 below.

TABLE 8

| Test Compound | Application Rate: PPM #/A | Percent Control 256 | 32 |
|---|---|---|---|
| Product of Example 1 | | 0 | 0 |

HOUSEFLY

Ten adult Houseflies are placed in a small (2"–3") wire screen cage fitted with a plastic cap. The cage is sprayed with the test compound at the desired concentration in the form of a solution prepared as described hereinabove. After spraying, the treated cages are stored until dry. Sixty minutes after spraying, readings are made of knock down. The cages are then placed on paper toweling moistened with 5–10% sucrose solution and stored on this toweling for 23 hours at which time the 24 hours-after-treatment mortality reading is taken. The results of this test are given in Table 9 below.

TABLE 9

| Test Compound | Application Rate: PPM | Percent Control 256 | |
|---|---|---|---|
| Product of Example 1 | k | 40 | |
| | m | 100 | |

Note:
k = 60 minute knockdown
m = 24 hour mortality

GERMAN COCKROACH

Solutions of test compounds are formulated as described hereinbefore and the solution which gives a desired application concentration is placed in a flask. Ten german cockroach adults are placed in a teaspoon tea strainer and are dipped into the test solution. The excess solution is shaken off, the tea strainer opened and the insects placed in a clear plastic container containing a small moist piece of dental wick. The container then is capped with a cover pierced with air holes. Insect mortality is observed 48 hours after the exposure. Results of this testing are indicated in Table 10 below.

TABLE 10

| Test Compound | Application Rate: PPM | Percent Control 256 |
|---|---|---|
| Product of Example 1 | | 0 |

SOUTHERN CORN ROOTWORM

A newly germinated corn seed is placed in a one ounce plastic cup fitted with a snap-on plastic lid and covered with approximately 5 grams of sterilized soil. The test compound is formulated into solutions as described hereinbefore and applied to the soil as a soil drench at the desired application rates. After application, the lids are snapped on the cups and the cups are allowed to stand for about 15 minutes to permit the solution to spread evenly through the soil. The lids are then removed, five second instar rootworm larvae are placed on the treated soil and the cups recapped. The cup is examined for insects mortality after 72 hours of exposure. Larvae which cannot crawl or right themselves are considered dead. Results of this testing are given in Table 11 below.

TABLE 11

| Test Compound | Application Rate: #/A | Percent Control | | | | |
|---|---|---|---|---|---|---|
| | | 16 | 1 | 0.5 | 0.25 | 0.125 |
| Product of Example 1 | | 100 | 20 | 0 | 0 | — |
| Product of Example 2 | | 90 | 70 | 20 | 30 | 30 |

YELLOW FEVER MOSQUITO

Solutions containing the test compound in the desired concentrations are formulated as described hereinabove. Each test solution is placed in a 10 ounce foamed polystyrene cup. Approximately ten 3–4 days old yellow fever mosquito larvae are placed in each test solution with an eyedropper. To each solution is then added a very small pinch of brewer's yeast and a very small piece of dry food (pulverized solid dog chow). Mortality data are taken after 48 hours of exposure. These data are shown in Table 12 below.

TABLE 12

| Test Compound | Application Rate: PPM | Percent Control | | | |
|---|---|---|---|---|---|
| | | 10 | 1.0 | 0.1 | 0.01 |
| Product of Example 1 | | 100 | 100 | 50 | 40 |

I claim:

1. A compound of the formula

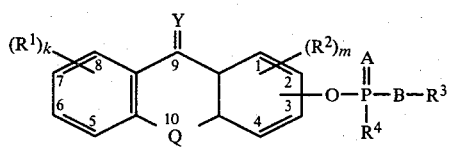

wherein $R^1$ and $R^2$ are each independently selected from the group consisting of halogen, alkyl, haloalkyl, nitro, alkylsulfinyl, alkylsulfonyl and cyano; k and m are integers from 0 to 3; Q is oxygen; Y is selected from the group consisting of oxygen and sulfur; $R^3$ is selected from the group consisting of alkyl and

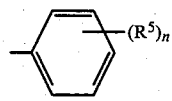

wherein $R^5$ is selected from the group consisting of halogen, alkyl, haloalkyl, nitro and cyano; n is an integer from 0 to 3; $R^4$ is selected from the group consisting of alkyl, alkoxy, alkylthio, amino, alkylamino, dialkylamino and

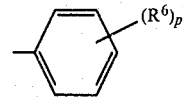

wherein $R^6$ is selected from the group consisting of halogen, alkyl, haloalkyl, nitro, and cyano; p is an integer from 0 to 3; and A and B are each independently selected from the group consisting of oxygen and sulfur, with the proviso that, if $R^4$ is alkoxy, then one of A and B must be sulfur.

2. The compound of claim 1 which is, O,O-diethyl O-(xanthen-9-one-2-yl) phosphorothionate.

3. The compound of claim 1 which is, O-ethyl O-(xanthen-9-one-2-yl) S-propyl phosphorothiolate.

4. The compound of claim 1 which is, O-ethyl O-(xanthen-9-thione-2-yl) S-propyl phosphorothiolothionate.

5. The compound of claim 1 which is, O-ethyl O-(xanthen-9-one-3-yl) S-propyl phosphorothiolothionate.

6. The compound of claim 1 which is, O-ethyl O-(7-nitroxanthen-9-one-2-yl) S-propyl phosphorothiolothionate.

7. The compound of claim 1 which is, O-ethyl O-(3-chloroxanthen-9-one-2-yl) S-propyl phosphorothiolothionate.

8. The compound of claim 1 which is, O-ethyl O-(7-cyanoxanthen-9-one-2-yl) S-propyl phosphorothiolothionate.

9. The compound of claim 1 which is O-ethyl O-(3-chloroxanthen-9-one-2-yl) S-propyl phosphorothiolate.

10. The compound of claim 1 which is O-ethyl O-(xanthen-9-thione-2-yl) S-propyl phosphorothiolothionate.

11. The compound of claim 1 which is O-ethyl O-(3-chloroxanthen-9-thione-2-yl S-propyl phosphorothiolate.

* * * * *

UNITED STATES PATENT OFFICE
CERTIFICATE OF CORRECTION

PATENT NO. : 4,299,772
DATED : November 10, 1981
INVENTOR(S) : James T. TRAXLER

It is certified that error appears in the above-identified patent and that said Letters Patent are hereby corrected as shown below:

In column 21, the first structure in Claim 1 should be as follows:

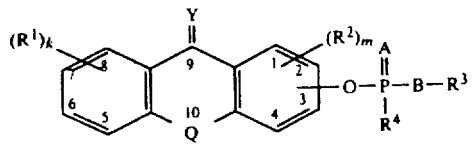

[SEAL]

Signed and Sealed this

Third Day of May 1983

Attest:

Attesting Officer

GERALD J. MOSSINGHOFF

Commissioner of Patents and Trademarks